(12) United States Patent
Nguyen

(10) Patent No.: US 10,220,157 B2
(45) Date of Patent: Mar. 5, 2019

(54) CAP FOR MEDICAL INJECTOR

(71) Applicant: Becton Dickinson France S.A.S., Le Pont-de-Claix (FR)

(72) Inventor: Emilie Nguyen, Garges-lès-Gonesse (FR)

(73) Assignee: Becton Dickinson France S.A.S., Le Pont-de-Claix (FR)

( * ) Notice: Subject to any disclaimer, the term of this patent is extended or adjusted under 35 U.S.C. 154(b) by 5 days.

(21) Appl. No.: 15/372,650

(22) Filed: Dec. 8, 2016

(65) Prior Publication Data

US 2017/0157332 A1 Jun. 8, 2017

Related U.S. Application Data

(60) Provisional application No. 62/264,529, filed on Dec. 8, 2015.

(51) Int. Cl.
*A61M 5/32* (2006.01)
*A61M 5/31* (2006.01)
*A61M 5/315* (2006.01)

(52) U.S. Cl.
CPC ........ *A61M 5/3204* (2013.01); *A61M 5/3137* (2013.01); *A61M 5/31511* (2013.01); *A61M 5/3202* (2013.01); *A61M 5/3213* (2013.01); *A61M 2005/3109* (2013.01)

(58) Field of Classification Search
CPC ............ A61M 5/3204; A61M 5/31511; A61M 5/3137; A61M 5/3202; A61M 5/3213
See application file for complete search history.

(56) References Cited

U.S. PATENT DOCUMENTS

| D239,021 S | 3/1976 | D'Alo | |
|---|---|---|---|
| 4,365,626 A | 12/1982 | House | |
| 4,636,201 A * | 1/1987 | Ambrose | ............ A61M 5/3202 604/192 |
| 4,832,695 A | 5/1989 | Rosenberg et al. | |
| 4,929,232 A | 5/1990 | Sweeney et al. | |
| 5,098,400 A * | 3/1992 | Crouse | ................ A61M 5/3204 604/192 |
| D337,157 S | 7/1993 | Ortiz | |

(Continued)

FOREIGN PATENT DOCUMENTS

| EP | 2886144 A1 | 6/2015 |
|---|---|---|
| EP | 2923716 A1 | 9/2015 |

(Continued)

*Primary Examiner* — Theodore Stigell
(74) *Attorney, Agent, or Firm* — The Webb Law Firm

(57) ABSTRACT

A medical injector including a cap remover or second cap is disclosed. The medical injector includes an injector housing defining a reservoir, a plunger rod, and a stopper engaged with a portion of the plunger rod and slidably disposed within the reservoir. The stopper being sized relative to an interior of the injector housing to provide sealing engagement with a sidewall of the injector housing. The medical injector further includes a needle having a sharpened first end and a second end in communication with the reservoir, a first cap covering the sharpened first end of the needle, and a second cap covering at least a part of the first cap. The second cap is engaged with the first cap such that removal of the second cap simultaneously removes the first cap from the first end of the needle.

13 Claims, 8 Drawing Sheets

(56) References Cited

U.S. PATENT DOCUMENTS

| | | |
|---|---|---|
| D375,788 S | 11/1996 | Potts et al. |
| D380,262 S | 6/1997 | Van Funderburk et al. |
| 5,647,849 A | 7/1997 | Kalin |
| D427,308 S | 6/2000 | Zinger |
| D473,646 S | 4/2003 | Baillargeon et al. |
| 6,582,397 B2 | 6/2003 | Alesi et al. |
| D483,487 S | 12/2003 | Harding et al. |
| D486,225 S | 2/2004 | Gay, III |
| D492,774 S | 7/2004 | Cindrich et al. |
| D497,990 S | 11/2004 | Jutila |
| D505,200 S | 5/2005 | Simpson et al. |
| 7,059,327 B2 | 6/2006 | Worthington |
| D605,755 S | 12/2009 | Baxter et al. |
| D607,558 S | 1/2010 | Abry et al. |
| D629,510 S | 12/2010 | Grunhut |
| D633,199 S | 2/2011 | MacKay et al. |
| D637,713 S | 5/2011 | Nord et al. |
| D642,261 S | 7/2011 | York et al. |
| D655,000 S | 2/2012 | Mirigian |
| D655,017 S | 2/2012 | Mosler et al. |
| D679,008 S | 3/2013 | Schroeder et al. |
| D681,230 S | 4/2013 | Mosler et al. |
| D702,343 S | 4/2014 | Dale et al. |
| D702,835 S | 4/2014 | Vinchon |
| D709,753 S | 7/2014 | Guala |
| 8,858,507 B2 | 10/2014 | Nielsen et al. |
| D718,439 S | 11/2014 | Woehr et al. |
| D738,494 S | 9/2015 | Kashmirian |
| D750,239 S | 2/2016 | Pappalardo |
| D750,258 S | 2/2016 | Crossley |
| D750,779 S | 3/2016 | Ahluwalia et al. |
| D751,192 S | 3/2016 | She et al. |
| D755,966 S | 5/2016 | Ahluwalia et al. |
| D755,967 S | 5/2016 | Ahluwalia et al. |
| D757,258 S | 5/2016 | Weibhaupt et al. |
| D757,935 S | 5/2016 | Solingen et al. |
| D760,891 S | 7/2016 | Nakamura et al. |
| D761,422 S | 7/2016 | Row et al. |
| D765,241 S | 8/2016 | Holland |
| D768,850 S | 10/2016 | Rozwadowski et al. |
| D768,851 S | 10/2016 | Rozwadowski et al. |
| 2001/0044606 A1 | 11/2001 | Inkpen et al. |
| 2004/0133172 A1 | 7/2004 | Wilkinson |
| 2004/0210197 A1 | 10/2004 | Conway |
| 2007/0129686 A1 | 6/2007 | Daily et al. |
| 2008/0228147 A1 | 9/2008 | David-Hegerich et al. |
| 2009/0105661 A1* | 4/2009 | Chevallier .......... A61M 5/3202 604/192 |
| 2009/0312705 A1 | 12/2009 | Grunhut et al. |
| 2011/0092915 A1 | 4/2011 | Olson et al. |
| 2012/0029439 A1 | 2/2012 | Hudson et al. |
| 2013/0085453 A1 | 4/2013 | Manke et al. |
| 2015/0045729 A1 | 2/2015 | Denzer et al. |
| 2015/0165129 A1 | 6/2015 | Row et al. |
| 2016/0144132 A1 | 5/2016 | Scanlon |
| 2016/0193428 A1 | 7/2016 | Perthu |
| 2017/0014578 A1 | 1/2017 | Bunch |

FOREIGN PATENT DOCUMENTS

| | | |
|---|---|---|
| WO | 03051423 A2 | 6/2003 |
| WO | 2005025636 A2 | 3/2005 |
| WO | 2010142812 A1 | 12/2010 |
| WO | 2011114917 A1 | 9/2011 |
| WO | 2014143815 A2 | 9/2014 |
| WO | 2014150201 A1 | 9/2014 |
| WO | 2014154498 A1 | 10/2014 |
| WO | 2014164943 A1 | 10/2014 |
| WO | 2015014363 A2 | 2/2015 |
| WO | 2015073740 A2 | 5/2015 |
| WO | 2015105511 A1 | 7/2015 |
| WO | 2015123096 A1 | 8/2015 |

* cited by examiner

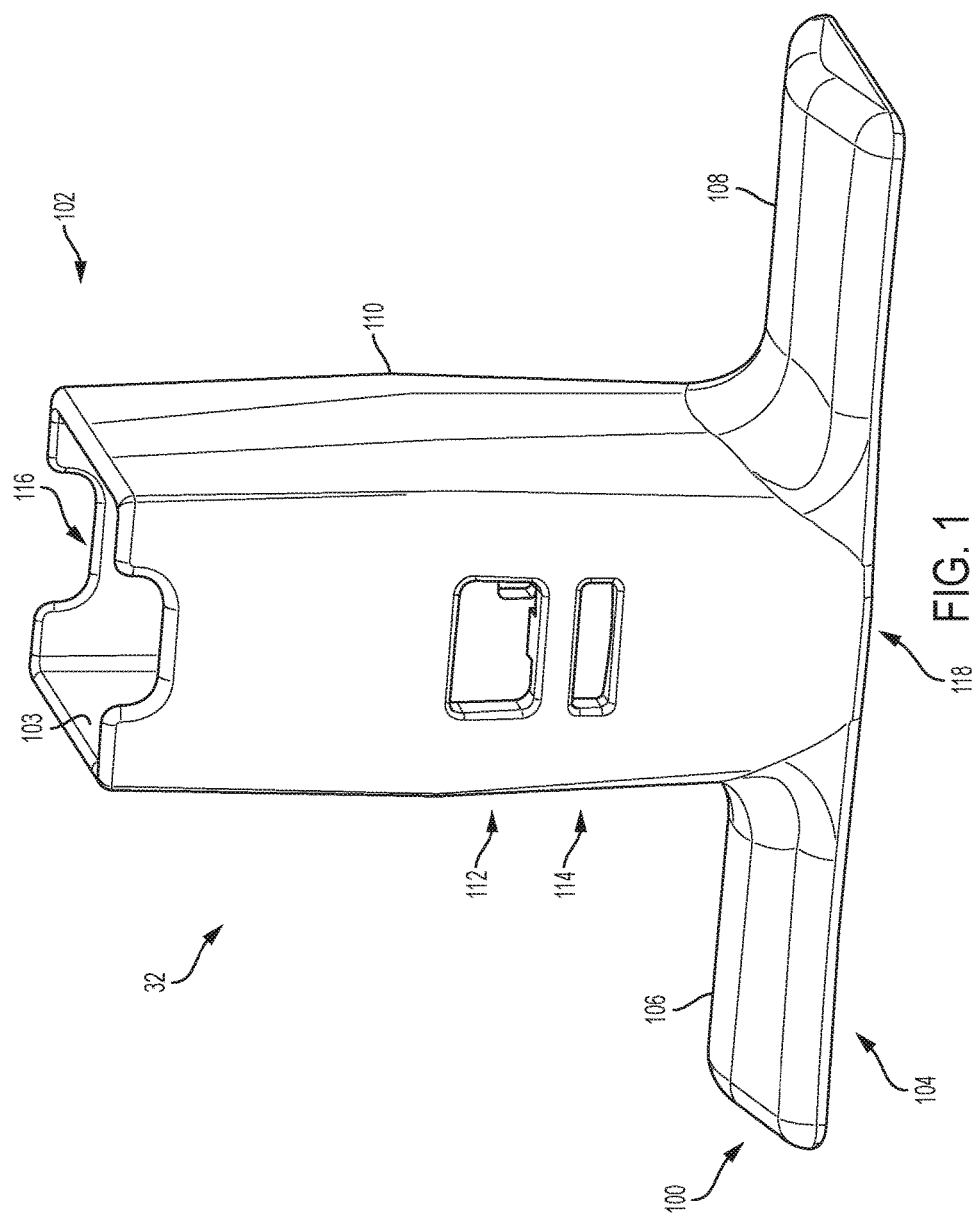

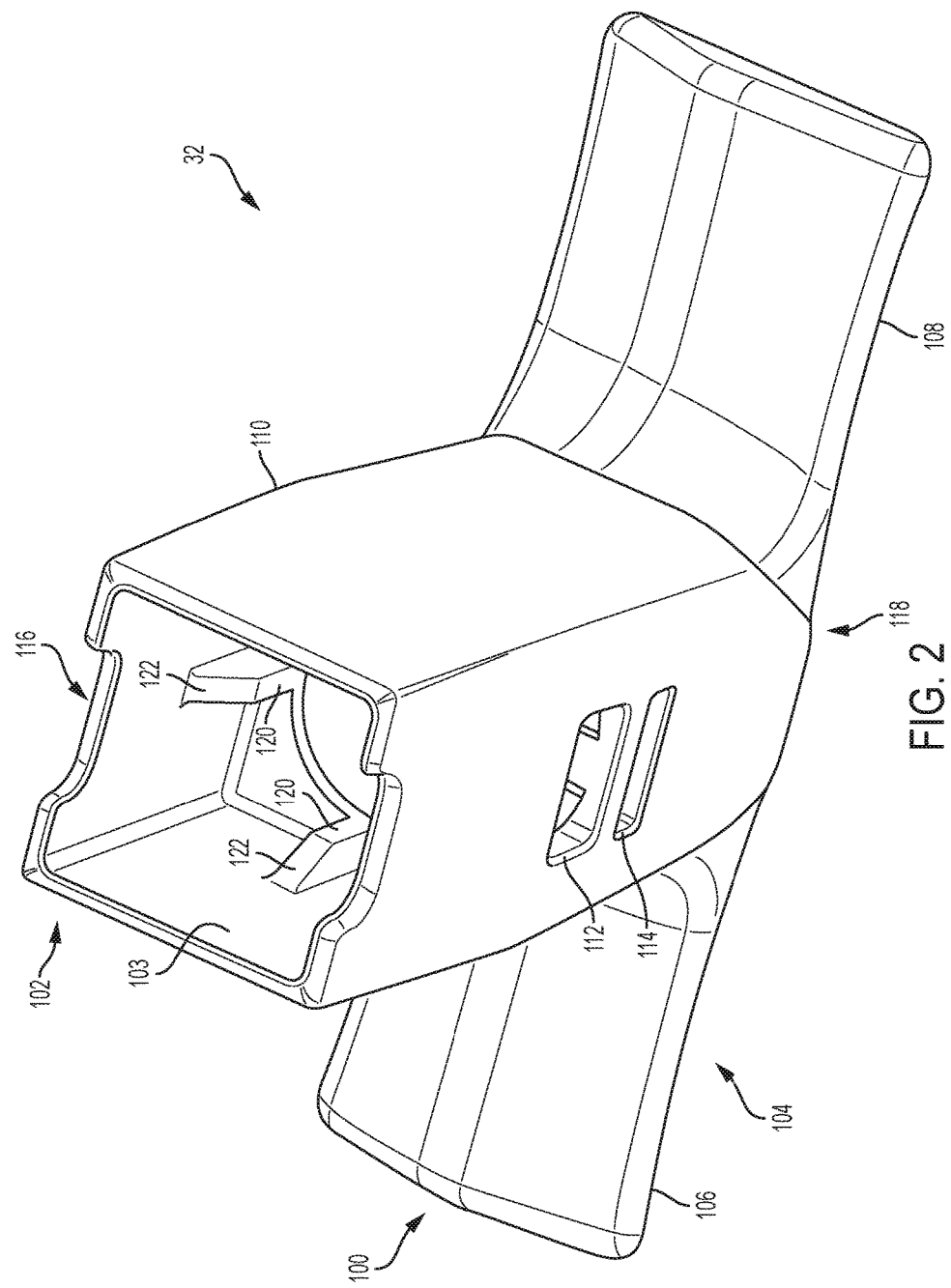

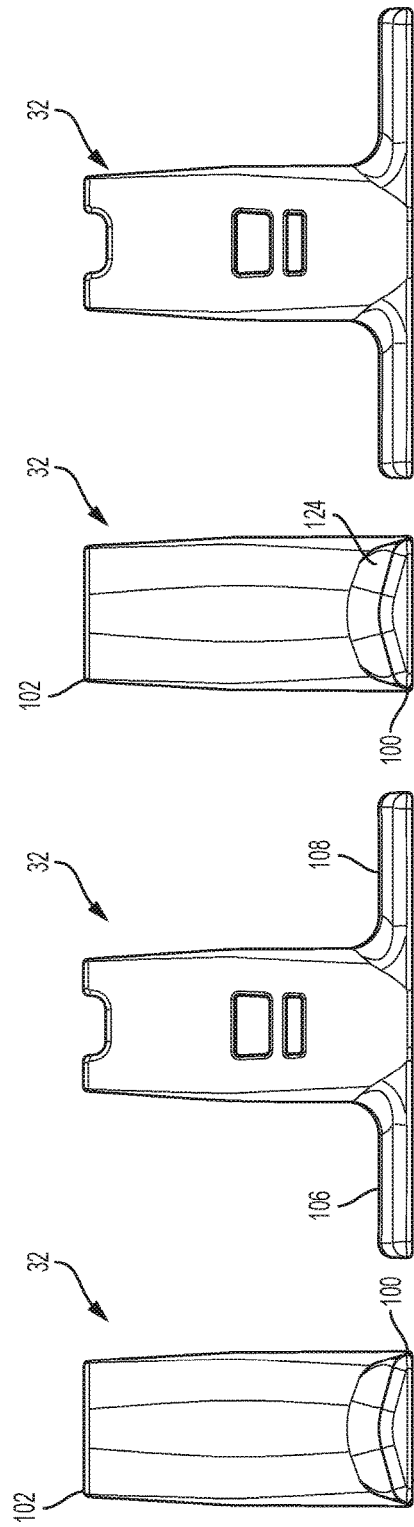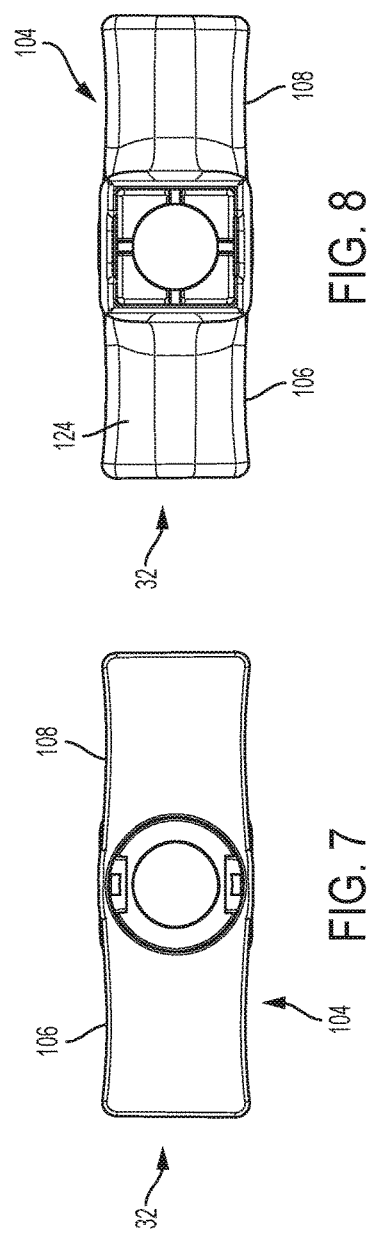

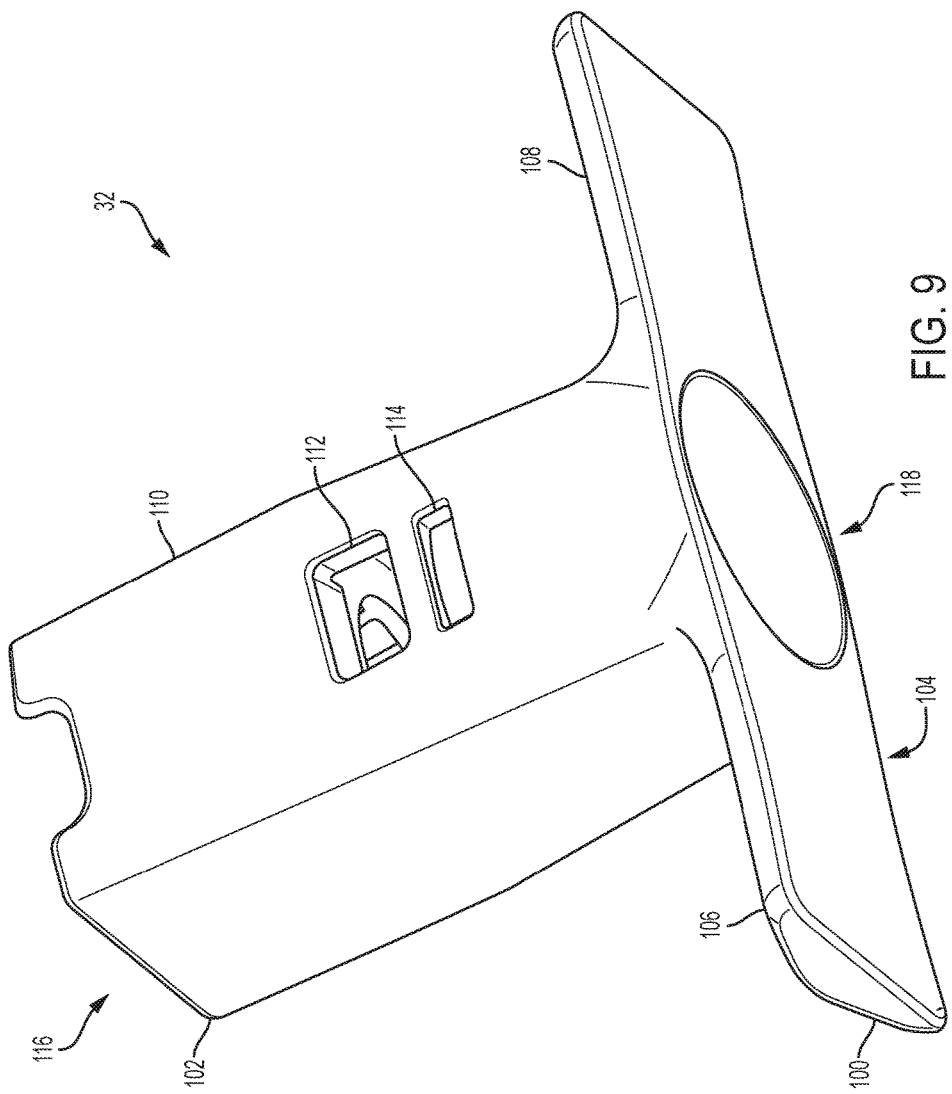

CAP FOR MEDICAL INJECTOR

CROSS-REFERENCE TO RELATED APPLICATIONS

This application claims the benefit of U.S. Provisional Application No. 62/264,529 filed Dec. 8, 2015, the disclosure of which is incorporated herein by reference in its entirety.

BACKGROUND OF THE INVENTION

Field of the Disclosure

The present disclosure relates generally to medical injector devices for delivery of a fluid or liquid medicament. More particularly, the present disclosure relates to a safety cap and/or a cap remover for a medical injector device or a syringe.

Description of the Related Art

Medical injectors and syringes are well known in the prior art. Medical injectors may include auto-injectors and pen injectors which are capable of delivering selected doses of fluids including liquid medicaments or vaccinations to a patient. Medical injectors typically are configured to receive a standard pre-filled glass or plastic syringe tipped with an injection needle. These devices may include a drive member for advancing a plunger into a syringe barrel to expel a liquid medicament out through the needle. The required manipulation of a standard prior art hypodermic syringe can be inconvenient, particularly where the injection is self-administered in a public environment, and many medication delivery pens, pen injectors, or other self-injectors have been developed to facilitate self-administration of injections.

In order to maintain sterility prior to use and to reduce the risk of incurring an accidental needle-stick, protection of the needle tip is important. Medical injectors are typically supplied with a rubber or plastic cap which guards the needle prior to use. Immediately prior to use, the user must remove the protective cap from the injector, such as by using the cap protector of the present invention.

SUMMARY OF THE INVENTION

In accordance with an embodiment of the present invention, a medical injector includes an injector housing defining a reservoir, a plunger rod, and a stopper engaged with a portion of the plunger rod and slidably disposed within the reservoir, the stopper being sized relative to an interior of the injector housing to provide sealing engagement with a sidewall of the injector housing. The medical injector further includes a needle having a sharpened first end and a second end in communication with the reservoir, a first cap covering the sharpened first end of the needle, and a second cap covering at least a part of the first cap. The second cap is engaged with the first cap such that removal of the second cap simultaneously removes the first cap from the first end of the needle. The second cap may engage the first cap via a friction fit.

The medical injector further includes an interior wall defining a cavity in a proximal end of the second cap, the cavity being sized and shaped to receive at least a portion of the first cap. A plurality of protrusions extend inwardly from the interior wall of the second cap and may be adapted to frictionally engage the first cap. At least one of the plurality of protrusions may include a tapered surface for aiding the second cap in receiving the first cap.

The first cap is formed from a first material and the second cap is formed from a second material. The first material is different from the second, material. In one embodiment the first cap is formed from an elastomeric sleeve disposed over at least the sharpened first end of the needle. The second material may be harder than the first material.

In one embodiment, a window may be defined through a sidewall of the second cap for visually viewing engagement of the second cap with the first cap. The medical injector may further include a liquid medicament disposed within the reservoir.

The second cap includes a body having a proximal end and a distal end, a first wing flange extending from a portion of the cap body in a first direction, a second wing flange extending from a portion of the cap body in a second direction, wherein the first direction is different from the second direction. The first and second wing flanges may extend from opposing sides of the cap body. The first and second wing flanges may each have a curved proximally directed surface and a substantially flat distally directed surface.

Also provided herein is a cap remover including a cap body having a proximal end and a distal end, and an interior wall defining a cavity within the proximal end of the cap body. A protrusion extends inwardly from the interior wall of the cap body. A first wing flange extends from a portion of the cap body in a first direction and a second wing flange extends from a portion of the cap body in a second direction. The first direction may be different than the second direction. The first wing flange and the second wing flange include a curved proximally directed surface and a flat distally directed surface.

In one embodiment, the protrusion includes a plurality of protrusions extending inwardly from the interior wall of the cap body. At least one of the plurality of protrusions may include a tapered proximal surface.

The cavity is sized and shaped to receive a needle cap covering a needle therein and the plurality of protrusions are adapted to frictionally engage the needle cap. With the plurality of protrusions of the cap body engaged with the needle cap, the cap remover may disengage the needle cap from the needle upon application of a distally directed force to the cap remover. A viewing window may be defined through a portion of the cap body.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 1 is a perspective view of a cap remover in accordance with an embodiment of the present invention.

FIG. 2 is a perspective view of a cap remover in accordance with an embodiment of the present invention.

FIG. 3 is a first elevation view of a cap remover in accordance with an embodiment of the present invention.

FIG. 4 is a second elevation view of a cap remover in accordance with an embodiment of the present invention.

FIG. 5 is a third elevation view of a cap remover in accordance with an embodiment of the present invention.

FIG. 6 is a fourth elevation view of a cap remover in accordance with an embodiment of the present invention.

FIG. 7 is a fifth elevation view of a cap remover in accordance with an embodiment of the present invention.

FIG. 8 is a sixth elevation view of a cap remover in accordance with an embodiment of the present invention.

FIG. 9 is a perspective view of a cap remover in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 10:
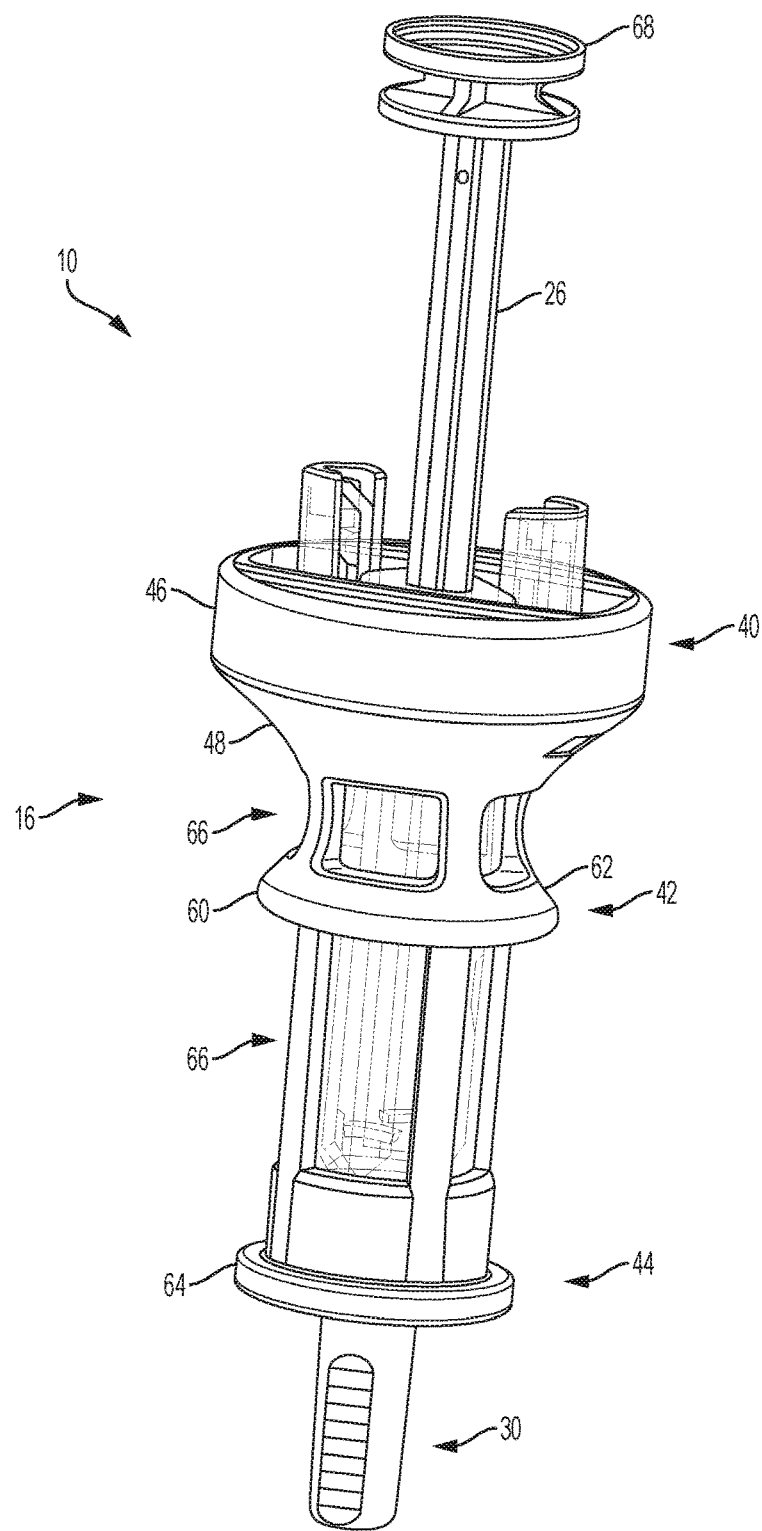
FIG. 10 is a perspective view of a medical injector with a cap in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a medical injector adapted for contact with a patient and/or engagement with a separate device, and "proximal" refers to the opposite direction of distal, i.e., away from the end of a medical injector adapted for engagement with the separate device. For purposes of this disclosure, the above-mentioned references are used in the description of the components of a medical injector in accordance with the present disclosure.

FIGS. 1-13 illustrate an exemplary embodiment of the present disclosure. Referring to FIGS. 1-9 and 13, a cap remover or a second cap 32 of the present disclosure is illustrated. Referring to FIGS. 10-13, in one embodiment, a medical injector 10 of the present disclosure includes a first cap 30 and a second cap or cap remover 32. For example, referring to FIG. 13, the second cap 32 can be secured to the medical injector 10 such that the second cap or cap remover 32 shields and covers a distal end 50 of a needle 14 and the first cap 30. Referring to FIG. 10, the first cap 30 shields and covers a distal end 50 of a needle 14. The first cap 30 may be formed of a plastic and/or rubber guard material. The second cap 32 may be formed from a harder material than the first cap 30. In one embodiment, the second cap 32 may be the only cap that shields and covers the distal end 50 of the needle 14.

In one embodiment, with the first cap 30 covering the distal end 50 of the needle 14 and with the second cap 32 covering the distal end 50 of the needle 14 and the first cap 30, the second cap 32 is engaged with the first cap 30 via a friction fit such that removal of the second cap 32 simultaneously removes the first cap 30 from the distal end 50 of the needle 14.

Figure 11:
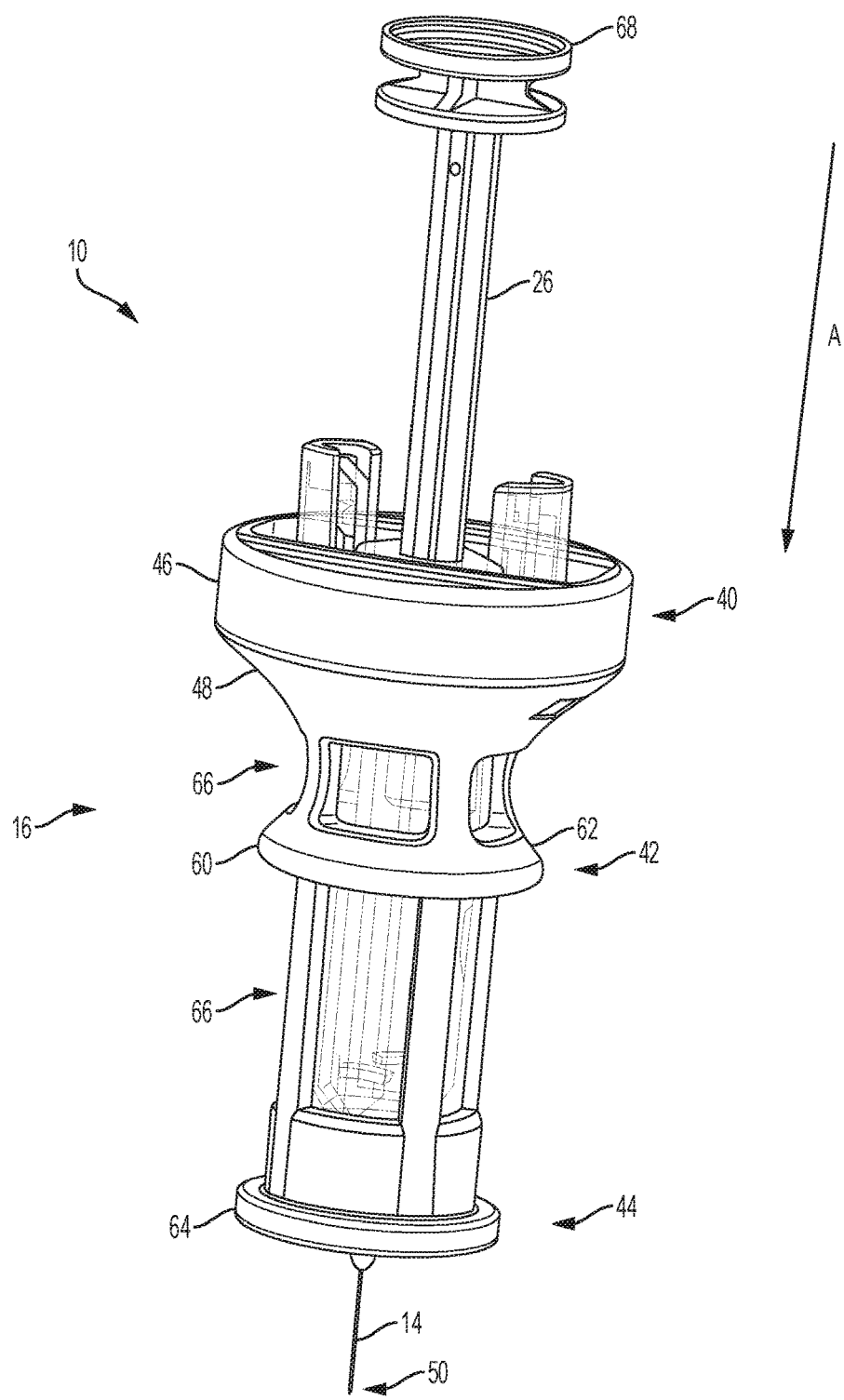
FIG. 11 is a perspective view of a medical injector in accordance with an embodiment of the present invention.
Figure 12:
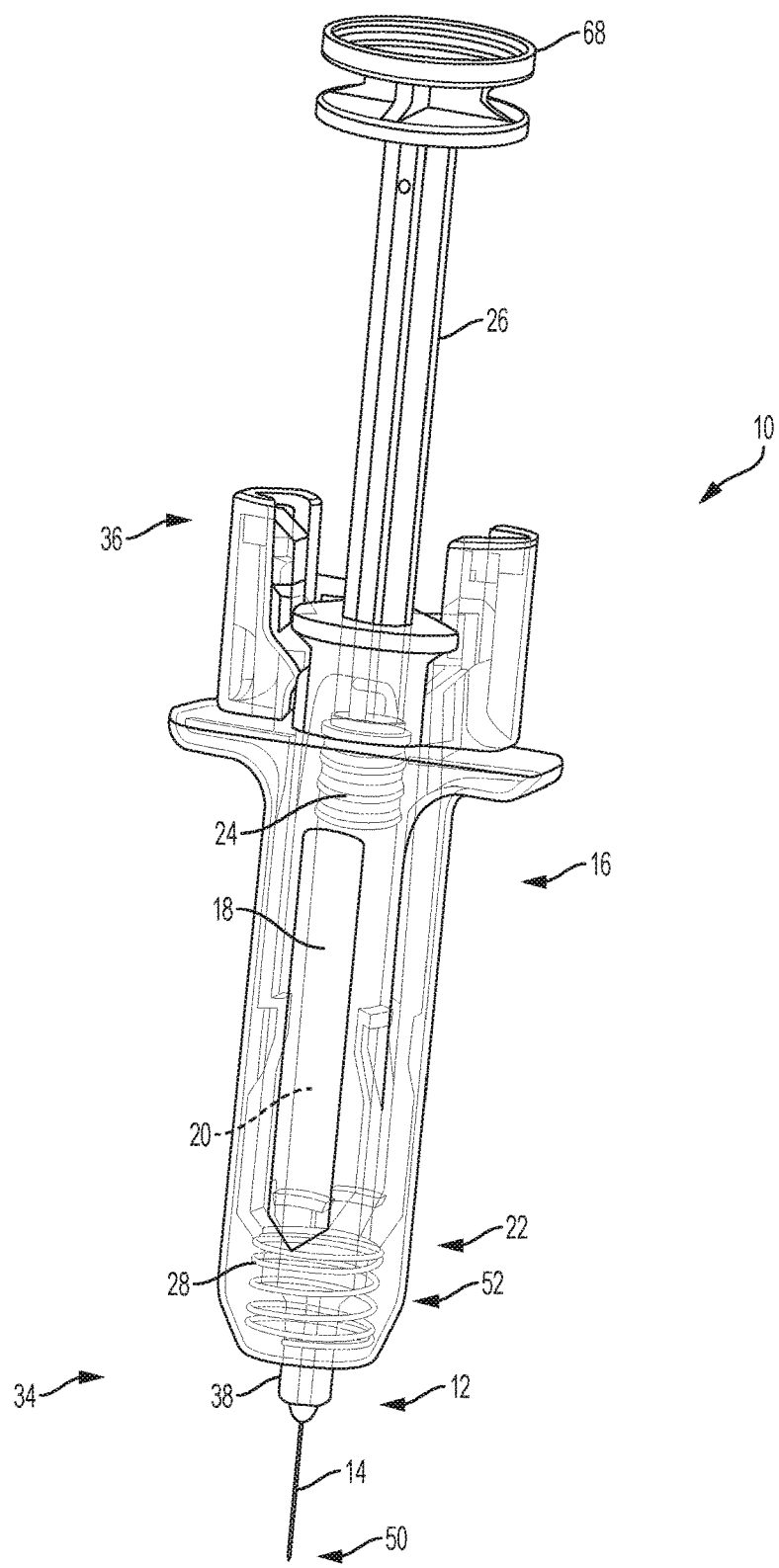
FIG. 12 is a cross-sectional view of a medical injector in accordance with an embodiment of the present invention.

Referring to FIGS. 10-12, a medical injector 10 includes a needle assembly 12 having a needle 14, an injector housing 16, a barrel 18 having a reservoir 20 for medicament sealed by a septum 22, a stopper 24, a plunger rod 26 having a flange 68, a spring 28, a first cap 30, and a second cap or a cap remover 32.

The medical injector 10 includes a distal end 34 and a proximal end 36. The reservoir 20 of the barrel 18 is encased within the injector housing 16. In one embodiment, the reservoir 20 may be defined by the injector housing 16. In another embodiment, the reservoir 20 may be defined by a separate component contained within the injector housing 16, e.g., a cartridge or barrel. The needle assembly 12 includes a needle 14 and a hub 38. The needle 14 includes a distal end 50, formed for insertion into a patient, and a proximal end 52.

The medical injector 10 of the present disclosure may be of various forms, including being a syringe, self-injector, auto-injector, or pen injector. In one embodiment, the medical injector 10 is well-suited for administering at least one fixed dose. In another embodiment, the medical injector 10 is well-suited for administering a series of fixed doses. The medical injector 10 may be configured in any way known to be compatible with the plunger rod 26. The medical injector 10 may include a reservoir 20 for accommodating an injectable medicament, which may be a drug cartridge or formed directly in the medical injector 10. The reservoir 20 may have one or more stoppers 24 associated therewith.

Referring to FIGS. 10-11, the injector housing 16 of the medical injector 10 includes an upper guard 40, a lower guard 42, and a base 44. The upper guard 40 includes a first flange 46 and a first tapered wall 48. In one embodiment, the upper guard 40 provides a gripping component that includes surfaces for accommodating a user's fingers, such as finger grip indentations or similar structure. For example, the upper guard 40 provides ergonomically shaped surfaces that substantially conform to a user's fingertips to aid the user in manipulating the medical injector 10 and using the medical injector 10 in a medical procedure, and may provide multiple finger grip positions for the user. The upper guard 40 allows a user to handle and/or grip the medical injector 10 in a variety of different ways.

The lower guard 42 includes a second flange 60 and a second tapered wall 62. The lower guard 42 provides a second gripping component that includes surfaces for accommodating a user's fingers, such as finger grip indentations or similar structure. In one embodiment, the lower guard 42 provides a user with vertical stability in hand, precisely during needle insertion with the medical injector 10.

The upper guard 40 and the lower guard 42 together provide a gripping component that includes surfaces for accommodating a user's fingers to aid the user in manipulating the medical injector 10 and using the medical injector 10 in a medical procedure.

The base 44 includes a flange 64 that contacts the skin of a user during use of the medical injector 10. The base 44 provides a stability component that stabilizes the medical injector 10 on a user's skin during use of the medical injector 10. In one embodiment, the base 44 also hides the spring 28.

Referring to FIGS. 10-11, the injector housing 16, the upper guard 40, the lower guard 42, and the base 44 are configured to provide viewing windows 66. The viewing windows 66 allow a user to see the barrel 18 that includes the medicament.

Figure 13:
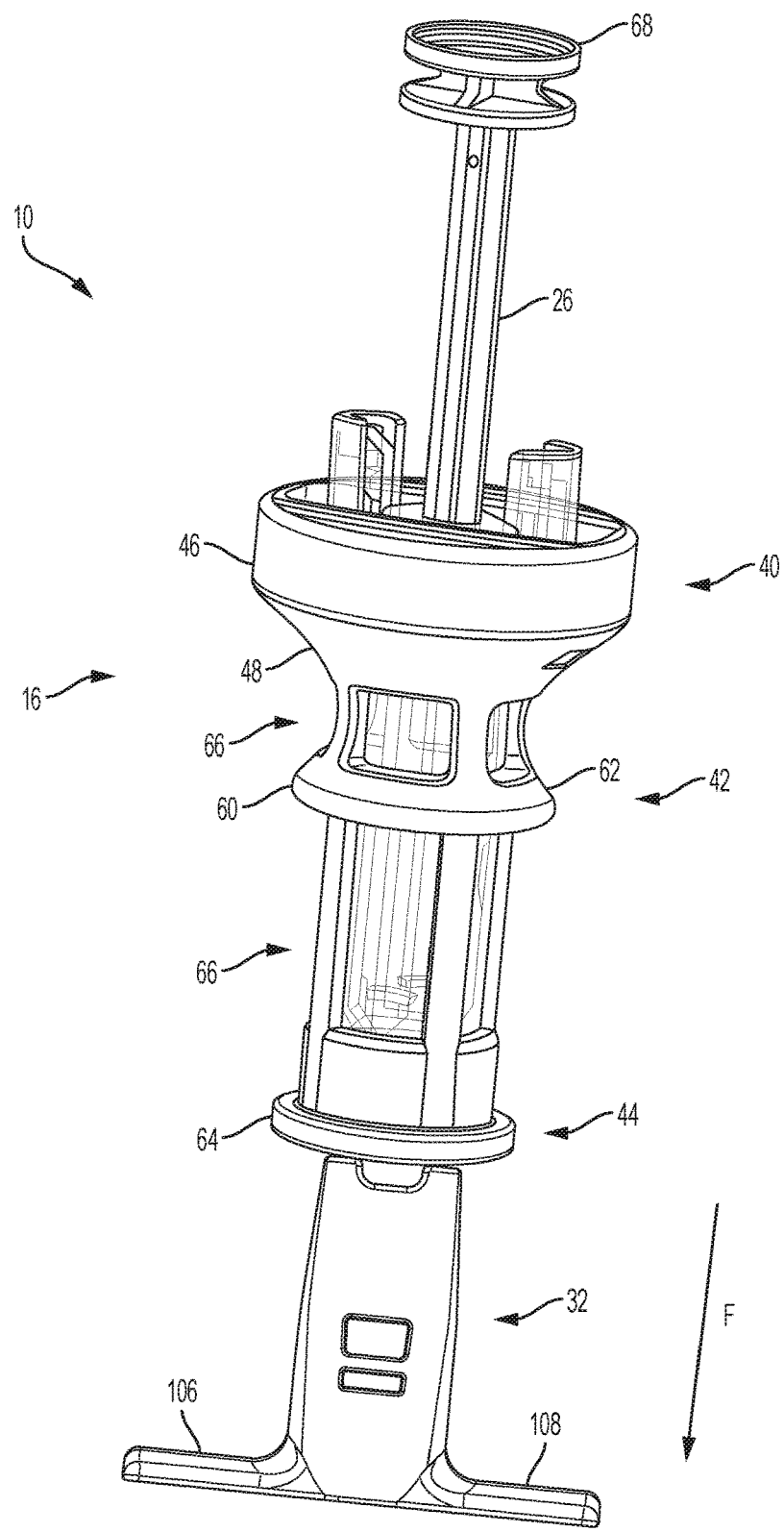
FIG. 13 is a perspective view of a medical injector with a cap remover in accordance with an embodiment of the present invention.

Referring to FIG. 10, a first cap 30 shields and covers the distal end 50 of the needle 14. Referring to FIG. 13, in one embodiment, the second cap or cap remover 32 shields and covers the distal end 50 of the needle 14 and the first cap 30. In one embodiment, the second cap 32 may be the only cap that shields and covers the distal end 50 of the needle 14.

Referring to FIGS. 1-9, the second cap or cap remover 32 includes a body 100 having a distal end 101, a proximal end 102, a distal flange 104 including a first wing flange 106 and a second wing flange 108, a sidewall 110, a first side aperture 112, a second side aperture 114, a cavity 116, a distal aperture 118, and ribs 120. Referring to FIGS. 1-9, in one embodiment, the second cap 32 has a generally upside down T-shaped body. In some embodiments, the first cap 30 is viewable through the side apertures 112, 114 or side viewing windows. In some embodiments, the two side apertures 112, 114 may be provided through the same or opposing sidewalls 110 of the second cap 32 for viewing engagement of the second cap 32 with the first cap 30.

Referring to FIG. 2, in one embodiment, an interior wall 103 of the body 100 defines a cavity 116 in a proximal end 102 of the body 100. The cavity 116 is sized and shaped to receive at least a portion of the first cap 30 therein. A protrusion or rib 120 may extend inwardly from the interior wall 103 toward a longitudinal axis L of the body 100. In one embodiment, the protrusion 120 is an annular rib. In another embodiment, the second cap 32 includes a plurality of ribs 120. The plurality of ribs 120 may include a tapered proximal surface 122. The proximal surface 122 may be angled from the interior wall 103 inwardly toward the longitudinal axis L of the body 100 and downwardly toward the distal end 101 of the body 100. The tapered proximal surface 122 aids the second cap 32 in sliding over the first cap 30 and securing the first cap 30 within the cavity 116. When the second cap 32 covers the first cap 30 the second cap or cap remover 32 shields and covers the distal end 50 of the needle 14 and the first cap 30.

With the first cap 30 covering the distal end 50 of the needle 14 and with the second cap 32 covering the distal end 50 of the needle 14 and the first cap 30, the second cap 32 is engaged with the first cap 30 via a friction fit such that removal of the second cap 32 simultaneously removes the first cap 30 from the distal end 50 of the needle 14. In one embodiment, the second cap or the cap remover 32 is removed from the medical injector 10 by applying a distally directed force F to the second cap or cap remover 32, as shown in FIG. 13.

In one embodiment, the second cap 32 provides a gripping component that includes surfaces for accommodating a user's fingers, such as distal flange 104 including a first wing flange 106 and a second wing flange 108 or similar structure. The first wing flange 106 and the second wing flange 108 may extend laterally from opposing sides of the body 100. The first wing flange 106 and the second wing flange 108 of the second cap 32 may provide ergonomically shaped surfaces that substantially conform to a user's fingertips to aid the user in removing the second cap 32 from the distal end 50 of the needle 14 and/or to aid the user in simultaneously removing the second cap 32 and the first cap 30 from the distal end 50 of the needle 14. For example, each of the first wing flange 106 and the second wing flange 108 of the second cap 32 may include a curved proximal surface 124 providing a user with multiple finger grip positions. The first wing flange 106 and the second wing flange 108 of the second cap 32 allow a user to handle and/or grip the second cap 32 in a variety of different ways. In one embodiment, the shape of the second cap 32 is designed to help disabled people more easily and more conveniently handle the second cap 32 and/or the medical injector 10. The first wing flange 106 and the second wing flange 108 of the second cap 32 may further include a substantially flat distal surface 126 such that the second cap 32 may be placed and rested on a flat surface.

In one embodiment, the first wing flange 106 and the second wing flange 108 of the second cap 32 allow a user to handle the second cap 32 without finger flexion. In one embodiment, the first wing flange 106 and the second wing flange 108 of the second cap 32 provide a gripping component that allows a user to better handle the second cap 32 and/or the medical injector 10.

When it is desired to use the medical injector 10 of the present disclosure, a user applies a removal force, such as a distally directed force to the second cap 32, to easily and simultaneously remove the first cap 30 from the distal end 50 of the needle 14. Referring to FIG. 11, with the caps 30, 32 removed, the distal end 50 of the needle 14 is exposed and ready to be positioned adjacent a desired portion of the skin of a user.

When it is desired to expel or deliver the medication contained within the barrel 18 of the medical injector 10, and with the medical injector 10 properly used to contact and pierce the skin of a user, the flange 68 of the plunger rod 26 and a portion of the injector housing 16 can be grasped, e.g., with the user's thumb on the flange 68 of the plunger rod 26 and with the user's fingers extending around the first flange 46 of the upper guard 40 of injector housing 16. In this manner, the medical injector 10 can be grasped by a user in a well-known and well-recognized manner similar to the operation of a conventional hypodermic syringe. Next, the user effects a squeezing movement between the thumb on the flange 68 of the plunger rod 26 and four fingers grasping the first flange 46 of the upper guard 40, thereby causing the plunger rod 26 to move in a direction generally along arrow A (FIG. 11).

Movement of the plunger rod 26 in the direction generally along arrow A actuates movement of the stopper 24 in the direction generally along arrow A toward the distal end 34 of the medical injector 10. In this manner, movement of the stopper 24 in the direction generally along arrow A forces the medicament fluid contained within the reservoir 20 of the barrel 18 to be forced out the distal end 50 of the needle 14 and into the user and/or patient.

After injection of the medicament fluid, the needle 14 can be removed from the skin of the patient. In one embodiment, the medical injector 10 may include an automatic retraction mechanism for moving the needle 14 into the injector housing 16 for safe shielding of the needle 14 after use. In one embodiment, the spring 28 may be used as part of the automatic retraction mechanism.

All of the components of the medical injector 10 may be constructed of any known material, and are desirably constructed of medical-grade polymers.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A medical injector comprising:
   an injector housing defining a reservoir;
   a plunger rod;
   a stopper engaged with a portion of the plunger rod and slidably disposed within the reservoir, the stopper sized relative to an interior of the injector housing to provide sealing engagement with a sidewall of the injector housing;
   a needle having a sharpened first end and a second end in communication with the reservoir;
   a first cap covering the sharpened first end of the needle; and
   a second cap covering at least a part of the first cap, the second cap comprising:
      a cap body having a distal end, a proximal end, and an interior wall;
      at least one protrusion extending inwardly from the interior wall adjacent the distal end;
      a first wing flange extending from the distal end of the cap body at the distal end in a first direction; and
      a second wing flange extending from the distal end of the cap body at the distal end in a second direction, wherein the first direction is different from the second direction,
   wherein the at least one protrusion of the second cap is engaged with the first cap such that removal of the second cap simultaneously removes the first cap from the sharpened first end of the needle.

2. The medical injector of claim 1, wherein the second cap engages the first cap via a friction fit.

3. The medical injector of claim 1, wherein the interior wall defines a cavity in the proximal end of the second cap body, wherein the cavity is sized and shaped to receive at least a portion of the first cap.

4. The medical injector of claim 3, wherein the at least one protrusion is a plurality of protrusions and wherein the plurality of protrusions are adapted to frictionally engage the first cap.

5. The medical injector of claim 4, wherein the at least one protrusion comprises a tapered surface for aiding the second cap in receiving the first cap.

6. The medical injector of claim 1, wherein a window is defined through a sidewall of the second cap for visually viewing engagement of the second cap with the first cap.

7. The medical injector of claim 1, wherein the first cap comprises a first material and the second cap comprises a second material, wherein the first material is different from the second material.

8. The medical injector of claim 7, wherein the second material is harder than the first material.

9. The medical injector of claim 1, further comprising a liquid medicament disposed within the reservoir.

10. The medical injector of claim 1, wherein the first cap comprises an elastomeric sleeve disposed over at least the sharpened first end of the needle.

11. The medical injector of claim 1, wherein the first and second wing flanges extend from opposing sides of the cap body.

12. The medical injector of claim 1, wherein the first and second wing flanges each comprise a curved proximally directed surface.

13. The medical injector of claim 1, wherein the first and second wing flanges each comprise a substantially flat distally directed surface.

* * * * *